(12) United States Patent
Odds et al.

(10) Patent No.: US 6,207,142 B1
(45) Date of Patent: Mar. 27, 2001

(54) COMPOSITIONS CONTAINING AN ANTIFUNGAL AND A CATIONIC AGENT

(75) Inventors: Frank Christopher Odds, Schilde; Roger Carolus Augusta Embrechts, Oud-Turnhout; Piet Richard Gudula De Doncker, Wilsele, all of (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 09/403,057

(22) PCT Filed: Apr. 7, 1990

(86) PCT No.: PCT/EP98/02144

§ 371 Date: Oct. 13, 1999

§ 102(e) Date: Oct. 13, 1999

(87) PCT Pub. No.: WO98/46207

PCT Pub. Date: Oct. 22, 1998

(30) Foreign Application Priority Data

Apr. 14, 1997 (EP) .................................................. 97201102

(51) Int. Cl.[7] ..................................................... A61K 7/075

(52) U.S. Cl. .......................................... 424/70.8; 424/70.1
(58) Field of Search ..................................... 424/7.01, 70.8

(56) References Cited

U.S. PATENT DOCUMENTS

| 5,132,107 | | 7/1992 | Lange . |
| 5,456,851 | | 10/1995 | Liu et al. . |
| 5,607,980 | * | 3/1997 | McAtee et al. . |
| 5,747,435 | * | 5/1998 | Patel . |

FOREIGN PATENT DOCUMENTS

| 399 858 A1 | 11/1990 | (EP) . |
| 468 856 A1 | 1/1992 | (EP) . |

* cited by examiner

*Primary Examiner*—Thurman K. Page
*Assistant Examiner*—P. E. McQueeney

(57) ABSTRACT

The invention relates to compositions such as body and hair cleansing products, in particular shampoos, comprising one or more antifungals inhibiting fungal ergosterol biosynthesis as a first active ingredient and 10'-undecen-3-oyl-aminopropyl trimethylammonium methylsulfate as a second active ingredient.

14 Claims, No Drawings

COMPOSITIONS CONTAINING AN ANTIFUNGAL AND A CATIONIC AGENT

CROSS REFERENCE TO RELATED APPLICATIONS

This application is a National Stage application under 35 U.S.C.371 of PCT/EP98/02144 filed Apr. 7, 1998, which claims priority from EP 97.201.102.7, filed Apr. 14, 1997.

The invention relates to compositions such as body and hair cleansing products, in particular shampoos, comprising one or more antifungals inhibiting fungal ergosterol biosynthesis as a first active ingredient, 10'-undecen-3-oyl-aminopropyl trimethyl-ammonium methylsulfate as a second active ingredient and as a cationic surface active agent, and art-known body or hair cleansing product ingredients as a carrier.

BACKGROUND OF THE INVENTION

Known medicated shampoos are, for example, the ketoconazole shampoos which are marketed in a 2% formulation and which show a beneficial effect in dandruff and seborrheic dermatitis after topical application. Ketoconazole was disclosed by Rosenberg et al. in U.S. Pat. No. 4,569,935 to be useful in the topical treatment of psoriasis and seborrheic dermatitis. Ketoconazole shampoos that exhibit better cosmetic attributes such as lathering and conditioning, and are acceptably stable to degradation so that they can be formulated to contain less than 2% active ingredient are disclosed in U.S. Pat. No. 5,456,851. Elubiol shampoos having a skin grease regulating action are known from WO-93/18743. WO-96/29983 discloses mild aqueous detergent compositions comprising from about 4 to about 12% by weight of an anionic surfactant, an amphoteric surfactant at a level of at least about 0.75 parts by weight per part by weight of said anionic surfactant, and one or more of 11 listed therapeutic agents. 10'-Undecen-3-oyl-aminopropyl trimethylammonium methylsulfate is a cationic surfactant commercially available under the Trademark Rewocid UTM 185, marketed by Rewo Chemische Werke GmbH, Steinau (Germany) and by Witco.

Prior art shampoos comprising anti-dandruff agents are designed in such a way that an optimum balance is achieved between efficacy and tolerability; the concentration of the active ingredient in the medicated shampoos is such that as many users as possible are effectively treated and as few as possible suffer adverse effects. Nonetheless, there remain substantial numbers of patients who do not benefit from using prior art shampoos, either because they do not respond to the treatment, or worse, because they do not tolerate the treatment with a particular medicated shampoo.

The number of patients not responding to particular medicated shampoo can be quite high (ketoconazole up to 30%; selenium sulfide up to 40%). Consequently, there is a hard felt need for new shampoos which provide effective anti-dandruff treatment for a larger proportion of number of patients using such a new shampoo; i.e. a new shampoo for which there are fewer non-respondents than with prior art shampoos.

On the other hand, patients suffering from dandruff or seborrheic dermatitis, as well as the authorities approving medicated shampoos, apply increasingly stricter criteria which such shampoos should meet. Amongst these criteria the most important are: absence of further aggravation of the condition due to the treatment, lowest possible incidence of side effects, further increase in the absence of symptoms such as irritation, pruritus and scaling (both adherent and loose scaling); improved cosmetic acceptability, in particular, good cleansing properties, absence of odour or stench, absence of staining or soiling of the clothes, and overall conditioning (wet and dry combing properties). Dandruff or seborrheic dermatitis are often accompanied by high or excessive oil or sebum production, and compositions having a beneficial effect thereon would clearly constitute a further advance in the treatment of dandruff.

Thus far, in order to achieve the above desiderata, most efforts have involved reformulating the shampoo base. There is, however, still a need for increasing the tolerability/acceptability of medicated shampoos, i.e. new shampoos are desired that are tolerated better by larger proportions of patients using such new shampoos.

DESCRIPTION OF THE INVENTION

The present invention relates to compositions such as body and hair cleansing products, in particular shampoos, comprising, consisting essentially of or consisting of one or more antifungals inhibiting fungal ergosterol biosynthesis as a first active ingredient, 10'-undecen-3-oyl-aminopropyl trimethylammonium methylsulfate as a second active ingredient, and art-known body and hair cleansing product ingredients as a carrier. In the following description, the invention is illustrated using shampoos as examples, but it will be evident to a person skilled in the art that the combinations according to the present invention can be utilized just as well in other body and hair cleansing products.

The combination of two differently acting anti-dandruff agents has two distinct advantages over the prior art shampoos which contain either of the active ingredients alone. First, the combinations act synergistically and as a consequence thereof, the concentration of one or both of the different types of agent can be lowered, thus increasing the tolerability. Secondly, an increased proportion of patients suffering from dandruff or seborrheic dermatitis respond to the shampoos according to the present invention. Each class of ingredients will now be discussed in turn.

The antifungal inhibiting fungal ergosterol biosynthesis is preferably an azole, an allylamine, or a mixture thereof. Preferred azoles are selected from the group comprising ketoconazole, econazole, elubiol, miconazole, itraconazole, fluconazole and mixtures thereof. Preferred allylamines are selected from the group comprising terbinafine, naftifine and mixtures thereof. The azole compounds ketoconazole, econazole and elubiol are most preferred because they harm the normal flora of the skin, in particular of the scalp, the least. Ketoconazole and elubiol are especially preferred as they produce a mutual synergistic effect on dermatophyte fungi when in used in combination with 10'-undecen-3-oyl-aminopropyl trimethylammonium methylsulfate (vide infra). Effective amounts of the antifungals in compositions according to the present invention are in the range of from about 0.1% to about 2.5% (w/w), and preferably from about 0.5% to about 1% (w/w). As will be explained further, at the lower end of this range, special precautions may have to be taken in order to ensure that the shampoo does not lose its efficacy due to degradation of the antifungal compound upon storage. Concentrations higher than those indicated do not improve the treatment of the conditions any further, and are on the whole more detrimental than beneficial.

The second active ingredient is 10'-undecen-3-oyl-aminopropyl trimethylammonium methylsulfate having the formula

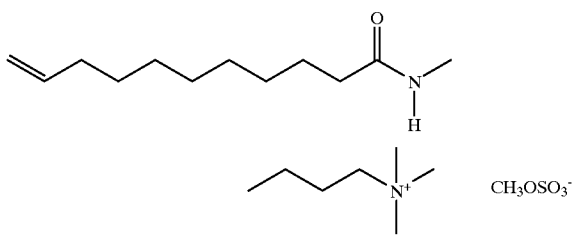

Its Chemical Abstracts registry number is [94313-91-4], its CTFA Adopted Name is Undecylenamidopropyltrimonium Methosulfate. This cationic surfactant is commercially available under the Trademark Rewocid UTM 185, marketed by Rewo Chemische Werke GmbH, Steinau (Germany) and by Witco. The commercial product is an aqueous formulation having a solids content in the range of 47 to 49%, appearing as a clear yellow liquid and giving a pH in the range of 5 to 7 when diluted to 1% in water.

Preferably, the first and the second active ingredients are present in quantities producing a mutual synergistic effect on the inhibition of the growth of dermatophyte fungi, in particular the species associated with dandruff and seborrheic dermatitis, i.e. *Malassezia furfur* (*Pityrosporum ovale*), but also other fungi such as *Epidermophyton, Microsporum*, Trichophyton species associated with, for example, dermatophytosis, pityriasis versicolor and the like. The ratio of the quantities of the first and the second active ingredient will depend on the nature of said active ingredients and on the target species. Particularly, it is contemplated that the weight:weight ratio between the first and the second active ingredient (antifungal:10'-undecen-3-oyl-aminopropyl trimethylammonium methylsulfate) may range from about 5:1 to about 1:150, in particular from about 1:1 to about 1:25. For example, and as already mentioned, ketoconazole and elubiol when in used in combination with 10'-undecen-3-oyl-aminopropyl trimethylammonium methylsulfate, in particular when used in a weight ratio ranging from about 1:1 to about 1:25, in particular in a weight range of about 1:20, produce a mutual synergistic effect on fungi, in particular on *Malassezia furfur*. Effective amounts of 10'-undecen-3-oyl-aminopropyl trimethylammonium methylsulfate in compositions according to the present invention are in the range of from about 0.04% to about 10% (w/w).

The shampoos according to the present invention can conveniently be formulated using art-known shampoo bases; the art-known shampoo ingredients comprise one or more of a surfactant, a foaming agent, a thickener, a preservative, an anti-oxidant, and acid or base or buffer sufficient to give the shampoo a pH in the range of from about 4 to about 10. A single ingredient can have two or more functions, e.g. surfactant and foaming agent, or antioxidant and buffer.

Many of the ingredients discussed hereinafter are commercially available in formulations (e.g. aqueous solutions), not as pure compounds. The amount of ingredient which can be used in preparing formulations according to the present invention are usually expressed as % (w/w) and refer to the amount of the commercially available product to be used, not the amount of pure product.

Suitable surfactants for use in the shampoos according to the present invention may be selected from the group comprising sodium $C_{14-16}$ olefin sulfonates, sodium lauryl sulfate, TEA lauryl sulfate, sodium laureth sulfate, cocamidopropylamine oxide, lauryl amine oxide, lauramido DEA, cocamidopropyl betaine, lauryl dimethyl betaine, cocodimethyl sulfopropyl betaine, sodium cocoyl sarcosinate, disodium oleamido MIPA sulfosuccinate, disodium cocamido MIPA sulfosuccinate, disodium laureth sulfosuccinate, cocoamphocarboxyglycinate, disodium oleamido MEA sulfosuccinate, amine glycinates, amine propionates and amine sultaines, and mixtures thereof. Preferably, a mixture of two or more different surfactants, in particular sodium laureth sulfate and sodium cocoyl sarcosinate; or sodium laureth sulfate and disodium laureth sulfosuccinate; or sodium lauryl sulfate, sodium laureth sulfate, TEA lauryl sulfate and cocamidopropyl betaine; may be used in the present shampoos. In the shampoos according to the present invention, the total amount of surfactants may range from about 36% to about 55% (w/w). Preferably, the weight of amphoteric surfactants is less than 15% by weight of the total amount of surfactants.

In the above definitions, and hereinafter, the term 'MEA' signifies a mono-ethanolamide of formula RCO-NH-$CH_2CH_2$-OH, the term 'DEA' signifies di-ethanol amide of formula RCO-N($CH_2CH_2$-OH)$_2$, 'TEA' signifies triethanolammonium; the term 'MIPA' signifies a mono-isopropanol amide of formula RCO-NH-$CH_2$-CHOH-$CH_3$; wherein each RCO-group is a fatty acid residue, such as a $C_{13-19}$alkylcarbonyl or $C_{13-19}$alkenylcarbonyl group.

Suitable foaming agents (foam boosters and stabilizers) for use in the shampoos according to the present invention may be selected from the group of fatty acid mono-and dialkanol-amides comprising cocamide MEA, cocamide DEA, oleamide MEA, oleamide DEA and mixtures thereof. The foaming agent may be present in a range from about 1 to about 10% (w/w), preferably from about 2 to about 6% (w/w), in particular about 4 to about 5% (w/w). These ingredients typically also have a thickening effect on the formulation.

Suitable preservatives for use in the present shampoos are dermatologically acceptable preservatives, e.g. tetrasodium or disodium EDTA, methylparaben, propylparaben, butylparaben, ethylparaben, imidazolidinyl urea, phenoxyethanol, quaternium 15, citric acid, preferably in combinations with one another. Tetrasodium and disodium EDTA, and citric acid also function as chelating agents.

As disclosed in U.S. Pat. No. 5,456,851, when the concentration of ketoconazole, or for that matter that of any other antifungal, is at the lower end of the ranges mentioned hereinabove, the addition of a carefully controlled amount of an antioxidant selected from the group consisting of butylated hydroxytoluene ("BHT"), butylated hydroxyanisole ("BHA"), ascorbic acid and N-acetyl-cysteine effectively stabilizes the ketoconazole or other azole present in the shampoo against degradation during accelerated aging for 13 weeks at 50° C., which is considered to be predictive of performance during storage at ambient temperatures for two years. Effective stability is considered to be a loss of active ingredient during storage of not more than about 10 percent. The proportion of BHT or BHA that has been found to be most effective is within the range of from about 0.01% to about 1% (w/w). Proportions greater than this amount do not stabilize ketoconazole as effectively for the 13-week accelerated aging period, although if one extends the accelerated aging period longer than 13 weeks, greater proportions of BHT or BHA tend to be more effective, since the BHT or BHA itself is also subject to degradation. However, it is well recognized by government regulatory agencies and in the pharmaceutical and cosmetic industries that stability testing for 13 weeks at 50° C. is quite sufficient to predict product stability during normal shelf life storage for two (2) years at room temperature. It is also equally important that, for safety reasons (that is, to minimize the potential for skin sensitization), it is desired to use as small an amount as possible of BHT or BHA.

Since shampoo users expect a shampoo to be slightly viscous, one or more thickeners are often included in the formulation which give it a viscosity in the range of 4,000 to 9,000 mPa.s at room temperature. A suitable thickener is a carbomer or polycarboxylic acid, such as Carbopol™ 1342 or Carbopol™ 1382, which is thickened by the addition of sodium hydroxide or sodium chloride at the end of the preparation. Other suitable thickeners are the foaming agents mentioned hereinabove, preferably cocamide MEA.

The shampoo may further comprise one or more pearlizing agents selected from the group consisting of ethylene glycol distearate, ethylene glycol monostearate and mixtures thereof, at a concentration of 0.0% to 2%; one or more plant extracts, e.g. from aloe, arnica, birch, bladder wrack, gentian, ginseng, hamamelis (witch hazel), hawthorn, kina, lemon, nasturtium, rosemary, tea tree and the like, at a concentration of from 0.0% to 5%; vitamins such as, for example, vitamin E (tocopherol) and derivatives, e.g. tocopheryl acetate, panthenol, and the like, at a concentration of 0.0% to 3%; antiinflammatory products of synthetic or natural origin, e.g. bisabolol, at a concentration of 0% to 5%; fragrances at a concentration of 0% to 2%; and one or more colorants.

The shampoo may further comprise from 0.0% to 10% of a conditioner such as polyquaternium-7, polyquaternium-10 or a similar cationic quaternary polymer, e.g. a quaternary silicone polymer. Also suitable are other silicone compounds such as polyalkyl siloxanes, polyalkyl arylsiloxanes, polyether siloxane copolymers and mixtures thereof. Polyalkyl siloxanes useful herein include, for example, polydimethylsiloxanes (PDMS). Polyalkylaryl siloxanes that may be used include polymethylphenylsiloxanes. Polyether siloxane copolymers that may be used include polypropyleneoxide modified polydimethylsiloxanes. Ethylene oxide or mixtures of ethylene oxide and propylene oxide may also be used. The water insoluble ones are preferred. Gums of the above described siloxane polymers are most desirable for use herein. These siloxane polymer gums are rigid as opposed to a liquid or fluid, with high mass molecular weights of from about 200,000 to about 1,000,000 and viscosities from about 100,000 mPa.s to about 150,000,000 mPa.s at 25° C. Polydimethyl siloxane gums are preferred. These gums have a viscosity of from about 100,000 mPa.s to about 150,000,000 mPa.s at 25° C. The gums selected for use herein have a viscosity such that when blended with a PDMS fluid the viscosity of the blend of gum and fluid falls within this range. Such PDMS fluids are used at levels from about 50% to about 60% of the total weight of said gum-fluid blend. Most preferred for the present invention is a blend containing from about 40% to about 60% PDMS fluid and from about 60% to about 40% PDMS gum. The preferred PDMS fluid is dimethicone fluid which has a viscosity of about 350 mPa.s at 25° C.

The pH of the shampoos according to the present invention are conveniently established using dermatologically acceptable acids, bases and buffers. The pH can range from about 4 to about 10, but preferably is in the range of about 6.5 to about 8, in particular from about 6.9 to about 7.4.

Some of the first active ingredients when at approximately neutral pH (pH 6 to 8), have limited solubility. In order to keep these agents homogeneously distributed throughout the shampoo, a suspending agent such as, for example, Avicel RC-591™ (a mixture of sodium CMC and microcrystalline cellulose) may be added. Several of the shampoo base ingredients, however, have considerable suspending properties of their own, and therefore the inclusion of particular suspending agents in the present shampoos is entirely optional.

The components of the shampoo are employed in conventional amounts, for example:

(a) 36% to 55% surfactants,
(b) 2% to 6% foaming agent,
(c) 0.1% to 2% antifungal,
(d) 0.05 to 2% 10'-undecen-3-oyl-aminopropyl trimethyl-ammonium methylsulfate salt
(e) 0.2% to 1.3% thickener,
(f) 0.01% to 1% BHT or BHA;
(g) preservatives sufficient to retard degradation of the final composition in order to give adequate shelf life,
(h) acid, base or buffer to yield a pH in the desired range, and
(i) water qs ad 100% (that is, sufficient water to make 100%).

EXAMPLES

In the following, a general process for preparing shampoos according to the present invention is presented. Suitable amounts for each of the ingredients can be derived from the preceding description and from the exemplary formulations shown in the tables hereinafter.

A vessel was charged with a 1.64% stock solution of Carbopol 1342 (prepared using a Quadro disperser which functions by keeping the powdered polymer evenly divided and pulling the powder by a vacuum into a stream of water) and deionized water, and heated to about 70° C. Both surfactants, i.e. sodium laureth sulfate and sodium cocoyl sarcosinate, were added, followed by the foaming agent, cocamide MEA, and a pearlizing agent (ethylene glycol distearate) and mixed until complete dissolution. Then the BHT was added and the mixture was stirred until complete dissolution thereof. The solution was allowed to cool slightly, whereupon the antifungal ingredient was added while stirring well. (The antifungal is added while the pH is slightly acidic, to facilitate dissolution.) Next, a 10'-undecen-3-oyl-aminopropyl trimethyl-ammonium methylsulfate was dispersed into the mixture and stirred until homogenously dispersed. The mixture was allowed to cool to about 40° C., at which temperature there were added the conditioner (polyquaternium-7), the preservatives quaternium-15 and tetrasodium EDTA, the colorants and fragrances, and the NaCl for thickening the solution. The pH of the solution was adjusted to 6.9–7.4 with a 25% aq. solution of NaOH and deionized water was added to the final volume. Similar shampoo formulations can prepared using analogous processes which will be apparent to the person skilled in the art.

Using the general procedures described above, the following shampoo formulations according to the present invention can be made; all quantities hereinafter are parts by weight.

The formulations according to the present invention are useful in the treatment of disorders such as dandruff, seborrheic dermatitis, the control of psoriasis, the reduction of oil or sebum production of the scalp, and the like disorders and discomforts. The formulations are to be applied topically to the affected body parts at regular intervals, in particular from at least once weekly to about once daily. Preferably they are employed more often in the beginning of the treatment, e.g. from 4 to 7 times a week, and less frequently in a later stage when the desired effect has been obtained and relapse is to be prevented (e.g. once or twice a week).

Example 1
Shampoo Formulations for Normal Hair (with conditioner)

| Ingredients | (a) | (b) |
|---|---|---|
| sodium laureth sulfate | 30 | 30 |
| sodium cocoyl sarcosinate | 10 | 10 |
| cocamide MEA | 4 | 4 |
| ketoconazole USP | 0.5 | 1 |
| 10'-undecen-3-oyl-aminopropyl trimethylammonium methylsulfate | 0.5 | 1 |
| glycol distearate | 1.25 | 1.25 |
| polyquaternium-7 | 1 | 1 |
| Carbopol ™ 1342 | 0.6 | 0.6 |
| tetrasodium EDTA | 0.5 | 0.5 |
| perfume oil | 0.5 | 0.5 |
| sodium chloride | 0.3 | 0.3 |
| sodium hydroxide 25% | 0.92 | 0.9 |
| butylated hydroxytoluene | 0.1 | 0.1 |
| quaternium-15 | 0.05 | 0.05 |
| colorants | 0.001 | 0.001 |
| deionized water qs ad | 100 | 100 |

Example 2
Shampoo Formulations for Oily Hair (with conditioner)

| Ingredients | (a) | (b) | (c) |
|---|---|---|---|
| sodium laureth sulfate | 33.33 | 33.33 | 33.33 |
| sodium cocoyl sarcosinate | 11 | 11 | 11 |
| cocamide MEA | 4 | 4 | 4 |
| ketoconazole USP | 0.5 | 0.75 | 1.2 |
| 10'-undecen-3-oyl-aminopropyl trimethylammonium methylsulfate | 0.5 | 0.25 | 0.8 |
| glycol distearate | 1.25 | 1.25 | 1.25 |
| polyquaternium-7 | 0.6 | 0.6 | 0.6 |
| Carbopol ™ 1342 | 0.75 | 0.75 | 0.75 |
| tetrasodium EDTA | 0.5 | 0.5 | 0.5 |
| perfume oil | 0.5 | 0.5 | 0.5 |
| sodium chloride | 0.3 | 0.3 | 0.3 |
| sodium hydroxide 25% | 1.18 | 1.243 | 1.18 |
| butylated hydroxytoluene | 0.1 | 0.1 | 0.1 |
| quaternium-15 | 0.05 | 0.05 | 0.05 |
| colorants | 0.0053 | 0.0053 | 0.0053 |
| deionized water qs ad | 100 | 100 | 100 |

Example 3
Shampoo Formulations for Dry or Damaged Hair (with conditioner)

| Ingredients | (a) | (b) | (c) |
|---|---|---|---|
| sodium laureth sulfate | 30 | 30 | 30 |
| sodium cocoyl sarcosinate | 10 | 10 | 10 |
| cocamide MEA | 4 | 4 | 4 |
| ketoconazole USP | 0.75 | 0.33 | 1 |
| 10'-undecen-3-oyl-aminopropyl trimethylammonium methylsulfate | 0.25 | 0.67 | 1 |
| glycol distearate | 1.25 | 1.25 | 1.25 |
| polyquaternium-7 | 5 | 5 | 5 |
| Carbopol ™ 1342 | 0.5 | 0.5 | 0.5 |
| tetrasodium EDTA | 0.5 | 0.5 | 0.5 |
| perfume oil | 0.5 | 0.5 | 0.5 |

-continued

| Ingredients | (a) | (b) | (c) |
|---|---|---|---|
| sodium chloride | 0.4 | 0.4 | 0.3 |
| sodium hydroxide 25% | 0.7333 | 0.733 | 1.19 |
| butylated hydroxytoluene | 0.1 | 0.1 | 0.1 |
| quaternium-15 | 0.05 | 0.05 | 0.05 |
| colorants | 0.0018 | 0.0018 | 0.0018 |
| deionized water qs ad | 100 | 100 | 100 |

In all the formulations given above in Examples 1–3, the proportion of sodium hydroxide may vary slightly, to arrive at the preferred pH level of 6.9 to 7.4, and the proportion of salt (NaCl) may vary, to arrive at the desired viscosity.

Example 4
Combination of 10'-undecen-3-ovl-aminopropyl Trimethylammonium Methylsulfate and Ketoconazole (with conditioner)

| Ingredients | Percent |
|---|---|
| purified water | 44.30 |
| sodium laureth sulfate | 15.00 |
| sodium lauryl sulfate | 10.00 |
| TEA lauryl sulfate | 12.00 |
| 10'-undecen-3-oyl-aminopropyl trimethylammonium methylsulfate | 2.10 |
| ketoconazole | 1.00 |
| methylparaben | 0.20 |
| propylparaben | 0.05 |
| cocamide MEA | 5.00 |
| ethylene glycol distearate | 1.25 |
| polyquaternium-7 | 3.00 |
| imidazolidinyl urea | 0.50 |
| cocamidopropyl betaine | 5.00 |
| citric acid | 0.35 |
| fragrance | 0.25 |
| | 100.00 |

Example 5
Combination of 10'-undecen-3-ovl-aminopropyl Trimethylammonium Methylsulfate and Elubiol (with conditioner)

| Ingredients | Percent |
|---|---|
| purified water | 44.30 |
| sodium laureth sulfate | 15.00 |
| sodium lauryl sulfate | 10.00 |
| TEA lauryl sulfate | 12.00 |
| 10'-undecen-3-oyl-aminopropyl trimethylammonium methylsulfate | 2.10 |
| elubiol | 1.00 |
| methylparaben | 0.20 |
| propylparaben | 0.05 |
| cocamide MEA | 5.00 |
| ethylene glycol distearate | 1.25 |
| polyquaternium-7 | 3.00 |
| imidazolidinyl urea | 0.50 |
| cocamidopropyl betaine | 5.00 |
| citric acid | 0.35 |
| fragrance | 0.25 |
| | 100.00 |

In the formulations given above in Examples 4 and 5, the proportion of citric acid may vary slightly, to arrive at the preferred pH level of 6.9 to 7.4.

Example 6
Ketoconazole (2.1% and 10'-undecen-3-oyl-aminopropyl Trimethyl-ammonium Methylsulfate 2% and 1% (w/w) Shampoos (without conditioner)

| | | |
|---|---|---|
| ketoconazole | 2.100 g | 2.100 g |
| 10'-undecen-3-oyl-aminopropyl trimethylammonium methylsulfate | 2.000 g | 1.000 g |
| imidazolidinyl urea | 0.200 g | 0.200 g |
| disodium laureth sulfosuccinate | 15.000 g | 15.000 g |
| cocamide DEA | 2.000 g | 2.000 g |
| hydrolized laurdimonium | 1.000 g | 1.000 g |
| macrogol 120 | 1.000 g | 1.000 g |
| perfume | 0.200 g | 0.200 g |
| hydrocloric acid | 0.400 g | 0.400 g |
| red erythrosine (FD & C No. 40) | 0.002 g | 0.002 g |
| sodium laureth sulfate | 38.000 g | 38.000 g |
| sodium hydroxide | 0.100 g | 0.100 g |
| sodium chloride | 0.500 g | 0.500 g |
| purified water | q.s. ad 100 g | q.s. ad 100 g |

Example 7
In vitro Synergisitic Inhibitory Effects Between Ketoconazole and 10'-undecen-3-oyl-aminopropyl Trimethylammonium Methylsulfate Aginst *Malassezia furfur*

Checkerboard interaction experiments involving nine isolates of *Malassezia furfur* (*M. furfur*) and the test substances with doubling dilution steps showed the combination of test substances to be highly synergistic.

Ketoconazole was dissolved in DMSO to give a stock solution containing 2000 µg/ml. 10'-undecen-3-oyl-aminopropyl trimethylammonium methylsulfate was diluted with ethanol to give a stock solution containing 2000 µg/ml. A series of six further 3.162-fold dilutions of each substances was prepared in the same solvent. (This dilution factor=SQRT(10), so that every second dilution was therefore a 10-fold dilution). Each of the seven concentrations of test substance was then further diluted in water to 12 times the final test concentration. An 8×8 checkerboard array of dilutions was next prepared in the wells of flat-bottomed, plastic microdilution plates with the ketoconazole dilution series arranged vertically and the dilutions of 10'-undecen-3-oyl-aminopropyl trimethylammonium methylsulfate arranged horizontally. Each well contained 10 µl of solution of each test substance. In an extra column of microdilution wells, 10 µl volumes of matching aqueous dilutions of the solvents alone were pipetted, to provide compound-free controls.

The panel of 9 *M. furfur* isolates used in the study was obtained from the fungal stock collection of the Department of Bacteriology and Mycology at the Janssen Research Foundation. All of the isolates were originally isolated from clinical material and three of them had been freshly isolated within 9 months prior to the study. The yeasts were maintained by subculture on a modification of the medium called "H. Dixon's formulation" by Van Abbe, N.J. (1964) [The investigation of dandruff. J. Soc. Cosmetic Chemists 15, 609–630]. This medium contained (per 1000 ml water): malt extract (Difco) 36 g; Mycological peptone (Oxoid) 6 g; Bacto-oxgall (Difco) 20 g; Tween 40 (Merck) 10 ml; glycerol (Difco) 2.5 ml; and Bacto-agar (Difco) 20 g. For use as a broth formulation the agar was omitted. Agar-based and broth versions of the medium were autoclaved for 5 min at 100° C.

Experimental inocula were prepared by incubation for 2 days at 30° C. in Dixon broth maintained in constant rotation at 20 rpm in test tubes angled at 5° from the horizontal. The broth cultures were standardized spectrophotometrically so they all gave an OD reading of 1.0 at 530 nm. These suspensions contained an average of $2 \times 10^6$ cells/ml as measured in agar plate counts. The yeasts were diluted 500-fold into Dixon broth to give suspensions containing $3–10 \times 10^5$ CFU/ml.

The inoculated medium was added in 100 µl volumes to the microdilution wells already containing dilutions of the test substances. The plates were sealed with adhesive stickers and incubated for 5 days at 30° C. The stickers were then removed and growth turbidity measured with the aid of a microplate reader as absorbance at 490 nm. For each combination of test substances nine microplates were run in parallel, each inoculated with a different *M. furfur* isolate. A tenth plate was set up inoculated with Dixon broth only, to provide negative control OD readings.

With the aid of a computer spreadsheet template, the $OD_{490}$ of each microplate well containing combinations of test substances, corrected for absorbance measured in the negative control plate, was expressed as a percentage of the mean $OD_{490}$ of the eight test substance-free positive control wells inoculated with *M. furfur*. The results were expressed in an 8×8 matrix and automatically shaded to indicate growth inhibition at or below 25% of control. In this way an indifferent interaction between two test substances would appear as a dark rectangle at the bottom right of the graphic, a synergistic interaction would appear as an inverted "L" shape at the bottom right of the graphic and an antagonistic interaction would appear as an extension of the rectangle towards the top left of the graphic. From the checkerboard results, minimal inhibitory concentrations (MIC) were determined as the lowest concentrations of test compounds, alone and in combination with other compounds, and fractional inhibitory concentrations (FIC) were calculated for each compound by the formula:

MIC(compound alone)/MIC(compound in presence of second compound)

The sum of the two FICs then gave a result of 1.0 for compounds with no interactive effect (indifference), <1.0 for compounds with a synergistic interaction and >1.0 for compounds with an antagonistic interaction.

Clearly positive results indicative of possible synergy were obtained with 10'-undecen-3-oyl-aminopropyl trimethylammonium methylsulfate (Rewocid UTM 185). The sum of the fractional inhibitory concentrations (FIC) for the combination ketoconazole and 10'-undecen-3-oyl-aminopropyl trimethylammonium methylsulfate against 9 *M. furfur* isolates in vitro was

| M. furfur isolate no. | FIC |
|---|---|
| B 39387 | 0.63 |
| B 45836 | 0.42 |
| B 45838 | 0.42 |
| B 58047 | 0.20 |
| B 58200 | 0.63 |
| B 58968 | 0.42 |
| J95-0821 | 0.42 |
| J95-0822 | 0.13 |
| J95-1435 | 1 |

The degree of synergy extended well beyond one-dilution effects that could have arisen by chance. The activity of 10'-undecen-3-oyl-aminopropyl trimethylammonium methylsulfate in combination with ketoconazole was therefore further investigated against the test panel of nine isolates, but with smaller (two-fold) dilution steps in the concentration series. The sum of the fractional inhibitory concentrations (FIC) for the combination ketoconazole and 10'-undecen-3-oyl-aminopropyl trimethylammonium methylsulfate against 9 *M. furfur* isolates in vitro was:

| M. furfur isolate no. | FIC |
|---|---|
| B 39387 | 0.50 |
| B 45836 | 0.26 |
| B 45838 | 0.13 |
| B 58047 | 0.25 |
| B 58200 | 0.19 |
| B 58968 | 0.25 |
| J95-0821 | 0.25 |
| J95-0822 | 0.12 |
| J95-1435 | 0.19 |

The results confirm unequivocally that both test compounds indeed interact synergistically with ketoconazole against *M. furfur* in vitro.

What is claimed is:

1. A body or hair cleansing composition comprising
   (a-1) one or more antifungals inhibiting fungal ergosterol biosynthesis as a first active ingredient,
   (a-2) 10'-undecen-3-oyl-aminopropyl trimethylammonium methylsulfate as a second active ingredient, and
   (b) art-known body or hair cleansing product ingredients as a carrier.

2. A composition according to claim 1 wherein the antifungal inhibiting fungal ergosterol biosynthesis is an azole selected from the group comprising ketoconazole, econazole, elubiol, miconazole, itraconazole, fluconazole, or a mixture thereof, or is an allylamine selected from the group comprising terbinafine, naftifine, or a mixture thereof.

3. A composition according to claim 2 wherein the first and the second ingredients are present in quantities producing a mutual synergistic effect on the inhibition of the growth of *Malassezia furfur*.

4. A composition according to claim 1 wherein the first ingredient is present in an amount ranging from about 0.1% to about 2.5% (w/w).

5. A composition according to claim 1 wherein the second ingredient is present in an amount ranging from about 0.04% to about 10% (w/w).

6. A composition according to claim 1 formulated as a shampoo.

7. A shampoo according to claim 6 wherein the art-known shampoo ingredients comprise one or more of a surfactant, a foaming agent, a thickener sufficient to give the final formulation a viscosity in the range of 4,000 to 9,000 mPa.s at room temperature, a preservative, an anti-oxidant, and acid or base or buffer sufficient to give the shampoo a pH in the range of from about 4 to about 10.

8. A shampoo according to claim 7 comprising one or more surfactants selected from the group comprising sodium $C_{14-16}$ olefin sulfonates, sodium lauryl sulfate, sodium laureth sulfate, cocamidopropylamine oxide, lauryl amine oxide, lauramido DEA, cocamidopropyl betaine, lauryl dimethyl betaine, cocodimethyl sulphopropyl betaine, sodium cocoyl sarcosinate, disodium oleamido MIPA sulfosuccinate, disodium cocamido MIPA sulfosuccinate, disodium laureth sulfosuccinate, cocoamphocarboxyglycinate, disodium oleamido MEA sulfosuccinate, amine glycinates, amine propionates and amine sultaines, and mixtures thereof.

9. A shampoo according to claim 7 wherein the foaming agent is selected from the group of fatty acid mono- and di-alkanolamides consisting of cocamide MEA, cocamide DEA, oleamide MEA, oleamide DEA and mixtures thereof.

10. A shampoo according to claim 7 wherein the antioxidant is butylated hydroxytoluene or butylated hydroxyanisole employed in an amount of about 0.01 to about 1% (w/w).

11. A shampoo according to claim 7 further comprising a conditioner.

12. A shampoo according to claim 7 further comprising one or more pearlizing agents selected from the group consisting of ethylene glycol distearate, ethylene glycol monostearate and mixtures thereof.

13. A shampoo according to claim 7 further comprising one or more fragrances and one or more colorants.

14. A process for preparing a shampoo formulation as defined in claim 7 comprising the steps of:
   (a) heating a solution of thickener and deionized water,
   (b) mixing the surfactants, the foaming agent and optionally the pearlizing agent with the solution of (a),
   (c) mixing the BHT with the solution of (b),
   (d) mixing the antifungal with the solution of (c),
   (e) dispersing the 10'-undecen-3-oyl-aminopropyl trimethylammonium methylsulfate in the mixture of (d),
   (f) allowing the suspension of (e) to cool somewhat and mixing therewith the preservative(s), the sodium chloride for thickening to the required viscosity, and optionally the conditioner, the fragrance(s) and colorant(s),
   (g) adding acid, base or buffer to the solution of (f) to yield a pH in the range of 4 to 10, and
   (h) adding deionized water to the solution of (g) to 100%.

* * * * *

UNITED STATES PATENT AND TRADEMARK OFFICE
CERTIFICATE OF CORRECTION

| | | |
|---|---|---|
| PATENT NO. | : 6,207,142 B1 | Page 1 of 1 |
| DATED | : March 27, 2001 | |
| INVENTOR(S) | : Frank Christopher Odds, Roger Carolus Augusta Embrechts and Piet Richard Gudula De Doncker | |

It is certified that error appears in the above-identified patent and that said Letters Patent is hereby corrected as shown below:

<u>Title page,</u>
Item [22], replace "[22] PCT Filed: Apri. 7, 1990" with
-- [22] PCT Filed: Apr. 7, 1998 --.

Signed and Sealed this

Twenty-first Day of January, 2003

JAMES E. ROGAN
*Director of the United States Patent and Trademark Office*